(12) United States Patent
Miquel Poblete et al.

(10) Patent No.: US 8,361,999 B2
(45) Date of Patent: Jan. 29, 2013

(54) METHODS OF TREATING CHOLESTEROL GALLSTONE DISEASE WITH EZETIMIBE

(75) Inventors: Juan Francisco Miquel Poblete, Talagante (CL); Flavio Nervi Oddone, Las Condes (CL); Atillio Gianpietro Gigotti Rivera, Huechuraba (CL); Silvana Zanlungo Matsuhiro, Providencia (CL)

(73) Assignee: Pontificia Universidad Catolica de Chile, Santiago (CL)

( * ) Notice: Subject to any disclaimer, the term of this patent is extended or adjusted under 35 U.S.C. 154(b) by 481 days.

(21) Appl. No.: 11/887,215

(22) PCT Filed: Apr. 4, 2006

(86) PCT No.: PCT/US2006/012449
§ 371 (c)(1),
(2), (4) Date: Aug. 25, 2009

(87) PCT Pub. No.: WO2006/107936
PCT Pub. Date: Oct. 12, 2006

(65) Prior Publication Data
US 2010/0016273 A1 Jan. 21, 2010

(30) Foreign Application Priority Data
Apr. 4, 2005 (CL) .................................. 762-2005

(51) Int. Cl.
*A61K 31/397* (2006.01)
(52) U.S. Cl. ................................. 514/210.02
(58) Field of Classification Search .................. None
See application file for complete search history.

(56) References Cited

FOREIGN PATENT DOCUMENTS

| WO | WO 94/17038 | 8/1994 |
|---|---|---|
| WO | WO 95/08532 | 3/1995 |
| WO | WO 04/000803 A1 | 12/2003 |
| WO | WO 04/000804 A1 | 12/2003 |
| WO | WO 04/000805 A1 | 12/2003 |
| WO | WO 04/001002 A2 | 12/2003 |
| WO | WO 2004/010948 A2 | 2/2004 |
| WO | WO 2004/081002 A1 | 9/2004 |

OTHER PUBLICATIONS

Miquel et al., Gastroenterology, (2006), A-816 (Abstract).*
Khairy et al., Saudi Medical Journal, (Sep. 2004), 25(9), pp. 1226-1228.*
Anonymous. "Zetia (Ezetimibe) Tablets." *Internet Article*—http://www.fda.gov/cder/foi/lable/2002/214451b1.pdf. Mar. 2003.
Anonymous. "Ezetrol." *New Zealand Data Sheet*—http://www.msd-newzealand.com/content/downloads/EZETROL_112005_DataSheet.pdf. Nov. 2005.
Rensen et al. Pederson et al. "Prospective study of malabsorption induced risk of gall stone formation in relation to fall in plasma cholesterol." vol. 29. No. 1. Jan. 1988. pp. 108-113. (Abstract).
Pedersen et al., "Turnover of plasma cholesterol in patients with cholesterol gallstones." vol. 197, No. 5. May 1975. pp. 421-425. (Abstract).
Koide et al. "Effect of CS-514, a competitive inhibitor of hydroxymethylglutaryl coenzyme A reductase on cholesterol gallstone formation in hamsters." vol. 1005, No. 1. Sep. 1989. pp. 65-71. (Abstract).
Duque et al.. "Inverse association between plasma cholesterol and gallstone disease." vol. 30, No. 3. May 1999. pp. 190-197. (Abstract).
A. Caroli et al., "Lipid pattern and plasma insulin in diabetics with gall stones", *Letters*, 1991, p. 339-340.
Scragg et al., "Plasma lipids and insulin in gall stone disease: a case-control study", *British Medical Journal*, vol. 289, 1984, p. 521-525.

* cited by examiner

*Primary Examiner* — Phyllis G. Spivack
(74) *Attorney, Agent, or Firm* — Merchant & Gould P.C.

(57) ABSTRACT

This invention discloses the use of compounds of the azetidinone family in treatment of cholesterol gallstone disease of the biliary tree in mammals. These drugs act by decreasing biliary cholesterol secretion, and at the same time increasing the biliary flow and the hepatic secretion of endogenous compounds (e.g. bile salts, phospholipids) into the bile, in turn, these endogenous compounds contribute to inhibiting precipitation and the formation of gallstones in the biliary tree.

10 Claims, 7 Drawing Sheets

METHODS OF TREATING CHOLESTEROL GALLSTONE DISEASE WITH EZETIMIBE

GENERAL DESCRIPTION AND BACKGROUND

1. Aim of the Invention

This invention discloses the use of compounds of the azetidinone family in the prevention or treatment of cholesterol gallstone disease of the biliary tree in mammals.

This invention is in the general area of lithiasic disease by cholesterol stones in the biliary tree. In particular, the invention evidences that the use of drugs that specifically block cholesterol intestinal absorption inhibit the onset of cholesterol gallstone disease in the biliary tree. These drugs act by decreasing biliary cholesterol secretion, and at the same time increasing the biliary flow and the hepatic secretion of endogenous compounds (e.g. bile salts, phospholipids) into the bile. In turn, these endogenous compounds contribute to inhibiting cholesterol precipitation and the formation of gallstones in the biliary tree.

2. Background of the Invention

Cholesterol gallstone disease in the biliary tree, specifically in the gallbladder (cholelithiasis), is a highly prevalent illness in the adult population of developed western countries (10 to 15% of the population over 18 years of age). This disease reaches epidemic levels in the Hispanic and Native American populations of most countries in the Andean area, including Chile, Peru, Bolivia and Mexico, among others (Carey and Paigen, 2002; Everhart et al., 2002). In Chile, for example, we have demonstrated that the general occurrence in males is of 17% and in women of 30%, reaching incidences of over 50% in the population over 50 years of age (Miquel et al., 1998a). It has recently been estimated that in the United States, approximately 20 million people had been affected or are currently affected by this disease (Everhart et al., 1999). In countries like Chile, there are more than 2 million habitants affected by cholelithiasis. This epidemiological scenario makes lithiasic disease of the biliary tree the digestive pathology with the highest social cost in countries like the United States, with a annual estimated cost of 8-10 billion dollars, in direct and indirect expenses, which amounts to 1.3-1.5% of the total health care costs (Everhart, 1994). On the other hand, in developing countries such as Chile, cholelithiasisis the first cause of surgical hospitalizations, only surpassed by obstetric hospitalizations, with a high social cost for all the country's health care services (Csendes et al., 1993; Medina, Pascual and Medina, 1983).

Biliary secretion has important physiological functions in our body; among other functions there is the elimination of steroidal molecules by secreting cholesterol and bile salts (catabolic cholesterol products). In fact, the biliary secretion is the main way of eliminating steroidal molecules from the body, having therefore, a central role in cholesterol homeostasis. The pathogenic mechanisms of cholesterol gallstone disease are only partially known. It is accepted as a dogma that the first metabolic defect necessary for the formation of gallstones is the generation of cholesterol rich bile, known as "cholesterol over-saturated bile", by the liver. The generation of cholesterol over-saturated bile is then a defect in the physiological functions of hepatic lipid metabolism (Carey, 1993; Miquel et al., 1998b). The main metabolic defect in people that develop cholesterol gallstones is the selective increment of cholesterol secretion into the bile, in relation with the molecules that can solubilize cholesterol in the bile (bile salts and phospholipids). Therefore, a thermodynamically unstable bile solution is generated where cholesterol tends to move from a soluble to an insoluble phase, with precipitation of cholesterol crystals and cholesterol gallstone growth, mainly in the gallbladder where local conditions favor stasis and the retention of cholesterol crystals (Apstein and Carey, 1996). It is assumed that there are genetic factors as well as environmental factors involved in the generation of this chronic metabolic disease. However, these factors have yet to be elucidated (Paigen, 2002). We need to emphasize that bile cholesterol is mainly preformed cholesterol derived from plasma lipoproteins and not originated from hepatic neo-synthesis. Nevertheless, it is not clear the participation of cholesterol from the diet (intestinal) and/or cholesterol derived from peripheral tissue to the liver (reverse transport of endogenous cholesterol) in the generation of over-saturated bile and finally of cholesterol gallstones (Paigen, 2002).

Once the gallstones are formed in the gallbladder they are clearly visible by imaging exams such as abdominal sonograms. The gallstones can remain in the gallbladder (or common bile duct) without causing symptoms during the person's whole life (silent gallstones), evolve to simple symptomatic forms (biliary colic type pain), or generate clinical complications with more serious prognosis like acute cholecystitis, vesicular empyema, suppurative cholangitis or acute pancreatitis, among others (Jonston and Kaplan, 1993). At the same time, cholelithiasis is the main risk factor for developing gallbladder cancer, a digestive neoplasia with bad prognosis and elevated prevalence in populations with high incidence of gallstone disease, like those present in Chile, Peru, Mexico, and the Native American and Hispanic populations of North America (Nervi, 2001).

The main risk factors associated with a higher frequency of cholelithiasis in the different populations studied are: female gender, Amerindian genetic background, cholelithiasis in first degree relatives, pregnancy, obesity or overweight in women, abrupt weight loss in the morbidly obese, bariatric surgery in the morbidly obese, diabetes mellitus, puerperium, prolonged fasting, total parenteral nutrition, hypertriglyceridemia (Amigo et al., 1999; Paigen, 2002; Wudel et al., 2002).

The animal models only develop cholelithiasis on the presence of a rich cholesterol diet (approximately 100-1,000 times that of the western human diet). Recently, some genetically manipulated animal models have demonstrated the critical role of the expression of genes relevant in intestinal cholesterol absorption (ACAT-2) and in transport of dietary cholesterol to the liver in the form of chylomicrons (Apolipoprotein E), in the generation of experimental cholelithiasis.

The liver is a central organ in the regulation of cholesterol homeostasis. It is the main organ involved in the synthesis and catabolism of plasma lipoproteins, and the only organ able to eliminate significant quantities of cholesterol (and other steroidal molecules) from the organism, either as free cholesterol (approximately 1 gr/day) (Grundy, 1983) or via its conversion or catabolism into bile salts (Dietschy, Turly and Spady, 1993). Defects in hepatic cholesterol metabolism cause two highly prevalent diseases, atherosclerosis and cholelithiasis. The hepatic cells have complex molecular mechanisms that finally regulate the homeostasis of intracellular cholesterol. Experimental evidence in humans and animals allowed to estimate that the cholesterol destined to biliary secretion is mainly (85-95%) preformed cholesterol generated by the uptake of plasma lipoproteins, and only 5-15% is generated by hepatic biosynthesis (Vlahcevic, 1994). Studies performed in lithiasic patients and controls show contradictory results related to the hepatic cholesterol neo-synthesis activity and bile salts neo-synthesis (review in Apstein and Carey, 1996; Carey, 1993). However, it is accepted that in lithiasic patients, the cholesterol destined to biliary secretion in abnormally high levels is preferentially originated from a preformed pool of lipoproteic origin. The influx of lipoprotein cholesterol towards the liver can come from two sources: a) by reverse transport of cholesterol from peripheral tissues to the liver in HDL and/or LDL (Fielding and Fielding, 1995) and b) cholesterol of exogenous origin (dietary) that is transported from the intestine to the liver fundamentally as remnants of chylomicrons (rQM) and very low density lipoproteins (VLDL) (Wilson and Rudel, 1994). It is important to mention that cholesterol adsorbed at the intestinal level can be of exogenous origin (from the diet) or endogenous (biliary cholesterol). In fact, there is evidence showing that cholesterol present in the bile and secreted into the intestine is qualitatively more relevant (1000 mg/day) that cholesterol present in the western diet (200-400 mg/day). At the same time, cholesterol present in the bile appears to be absorbed more efficiently than dietary cholesterol. Other evidence suggest that in humans, dietary or intestinal cholesterol could be very relevant in the generation of lithogenic bile in people genetically predisposed to develop this disease. Most of the cholesterol deposited in gallstones seems to have a dietary origin (Holzbach, 1984). In addition, other evidence support the idea that cholesterol of intestinal origin is preferentially destined to biliary secretion facilitating the formation of lithogenic bile (Cooper, 1991). For example, a cholesterol enriched diet in gallstone carriers significantly increases the biliary cholesterol content in the subsequent weeks (Kern, 1994). There is only one repot that has compared the effect of dietary cholesterol in gallstone women and controls, demonstrating that only gallstone patients increase the biliary cholesterol secretion when exposed to an exogenous overcharge of dietary cholesterol (Kern, 1994). This data suggests that dietary cholesterol that can be destined to biliary secretion is probably regulated by yet unidentified genes, and their regulatory mechanisms appear to be altered in patients that develop gallstone disease.

In contrast to the almost complete intestinal absorption of the majority of other nutrients, cholesterol absorption is limited to an average of 40-60% of the ingested cholesterol, with great variability among different species (Jolley, Dietschy and Turley, 1999) and amid people (Gylling and Miettinen, 2002b). The variability in cholesterol absorption capacity among individuals can be as high as 4-6 times (in a range of 30-80%) for a similar amount of dietary cholesterol. This finding contrast with the intra-individual variations observed at different times under the same dose of dietary cholesterol (<6%) (Bosner et al., 1993). Similar variations in dietary cholesterol absorption ability can be observed in animal models, especially among different mice strains (Jolley et al., 1999). In the last few years, this variability in the capacity to adsorb dietary cholesterol has attained great relevance, not only from the viewpoint of studying the physiology of cholesterol metabolism, but also from the perspective of designing more effective therapeutic alternatives for the treatment of dyslipidemias and atherosclerosis (Gylling and Miettinen, 2002a). During the last years, it has been possible to unravel, at least partially, the molecular mechanisms that control and regulate cholesterol intestinal absorption (Klett and Patel, 2004).

The development of compounds that interfere with cholesterol absorption has gain great relevance during the last years with the aim of developing strategies for the treatment of hypercholesterolemias and atherosclerosis. The compounds that have been evaluated can be classified in three categories depending on their site of action: A) Those that interfere with intestinal absorption at the intra-luminal level, such as resins like cholestyramine, and natural and synthetic saponines, B) drugs that interfere with the entry of cholesterol into the enterocyte, such as type 2-azetidinones (Ezetimibe) and C) drugs that interfere with the esterification of cholesterol incorporated into the enterocyte, specifically inhibiting the enzyme ACAT-2. Only the compounds mentioned in point A and the 2-azetidinones are currently used in clinical practice for the treatment of dyslipidemias and prevention of cardiovascular diseases.

EZETIMIBE (SCH 58235, ((−)-1-(4-fluorophenyl)-(3R)-[3-(4-fluorophenyl)-(.S)-hydroxypropyl]-(4S)-(4-hydroxyphenyl)-2-azetidinone)) is the first drug in a group of hypocholesterolemic medicines, the specific inhibitors of cholesterol absorption (Klett and Patel, 2004), derived from the structural class of the 2-azetidinones. It was approved by the US Food and Drug Administration in October 2002, under the registered brand Ezetrol®-MSD-Schering-Plough; and Zetia®, Merck/Schering Plough, North Wales, Pa. Ezetimibe (SCH 58235) corresponds to the second generation of specific inhibitors of cholesterol intestinal absorption, and was generated by structural modification and metabolites of SCH 48461 and SCH 53695 (SCH 53695 is the C-4 phenol of SCH 48461). Ezetimibe is a metabolite derived from the active forms of SCH 48461, with an inhibitory activity in cholesterol absorption 400 times higher than its predecessor analog (SCH 48461). This increase in the inhibitory activity of cholesterol absorption has been attributed to the incorporation of phenolic rings into SCH 48461 (Jeu and Cheng, 2003). Ezetimibe has demonstrated to effectively inhibit intestinal cholesterol absorption in mammalian models (murine models) in dosages that fluctuate between 0.1-6 mg/kg body weight per day. Ezetimibe is indicated to be used as monotherapy or as combined therapy with inhibitors of the HMG-CoA-reductase (statins) in the treatment of primary hypercholesterolemias for the reduction of total cholesterol, LDL cholesterol and ApoB. It is also indicated as combined therapy in patients with homozygous familial hypercholesterolemia, and as monotherapy in patients with homozygous familial sitosterolemia (Cheng and Leiter, 2003; Davidson, 2003; Iglesias and Diez, 2003; Lipka, 2003). The combined therapy with 2-azetidinones associated to inhibitors of the HMG-CoA-reductase (statins) such as pravastatin, simvastatin, rosuvastatin, lovastatin, fluvastatin, atorvastatin and cerivastatin, is based in the selective inhibition of cholesterol intestinal absorption. Because of this, a reduction in the hepatic cholesterol content triggers a compensatory associated effect in humans, increasing the neo-synthesis of cholesterol at the hepatic level. Therefore, when the 2-azetidinones are associated with a selective inhibitor (statins) of the critical enzyme (HMG-CoA-reductase) in the cholesterol neo-synthesis pathway, the reduction in the plasma cholesterol is enhanced. The combined therapy with 2-azetidinones plus inhibitors of the HMG-CoA-reductase in the pathology concerned in this invention (cholelithiasis) has not been evaluated and there are no communications about it in the scientific and medical literature.

The specific mechanism of Ezetimibe action as a selective inhibitor of cholesterol absorption is still not known in detail. It is hypothesized that it acts by inhibiting the entry of cholesterol from the lumen into the enterocyte, acting at the apical plasma membrane level and interacting with some proteins involved in cholesterol trafficking (Klett and Patel, 2004). Ezetimibe is incorporated into the enterocyte, is glucuronized into its active metabolite at this level, and enters the entero-hepatic circuit of lipids (Jeu and Cheng, 2003). Even though Ezetimibe is up taken with high affinity by the liver, and is actively secreted toward the biliary tree reaching elevated concentrations in the bile, it is not known if this drug has other additional functions in the transport of steroidal molecules (e.g. cholesterol) at the hepatic and biliary tree levels.

It is universally accepted today that the only effective therapy for the treatment of gallstone disease is the surgical resection of the gallbladder with its gallstones (cholecystectomy) (Gui et al., 1998). However, some pharmacological alternatives for treatment (non-surgical) have been developed. These treatments demonstrated effectiveness in the dissolution of gallstones in specific subgroups of patients with cholelithiasis (Hillebrant et al., 2002; Stiehl et al., 1984) and in some specific groups of patients at high risk for developing gallstone disease (Mason and Renquist, 2002; Wudel et al., 2002).

The medical alternative is the dissolution of cholesterol gallstones by bile salts, chenodeoxycholic and ursodeoxycholic acid (Sugata, 1993). The most utilized internationally has been ursodeoxycholic acid because it shows lower rates of adverse effects and similar efficacy. These drugs act by increasing the bile salts contents in the bile and decreasing hepatic cholesterol secretion, thus generating bile that is not supersaturated with cholesterol and allowing the solubilization of cholesterol gallstones. It was demonstrated to be an affective therapy in patients with small cholesterol gallstones. However, it requires long therapy periods (6-12 months) and it is associated with high recurrence levels (50% in 5 years) when discontinued (Bilhartz, 1998; Stiehl et al, 1984). The association of ursodeoxycholic acid with statins (inhibitors of cholesterol neo-synthesis) has also been explored to this same end, but the efficacy of the therapy has not been demonstrated (Hillebrant et al., 2002; Miettinen et al., 1998).

The possible utility of other hypolipaemiant drugs in the treatment of cholesterol gallstone disease has been evaluated without any clinical demonstrated effect. The use of fibrates, niacin or resins that decrease cholesterol and bile salts intestinal absorption (cholestyramine, probocol), has demonstrated no therapeutic effectiveness in cholesterol gallstone disease patients. Moreover, the use of hypolipaemiant therapies (that decrease plasma cholesterol) with fibrates (specifically clofibrates) in humans shows a clear increase in the risk of developing cholelithiasis (Amigo et al., 1999; Apstein and Carey, 1996). On the other hand, the use of HMG-CoA-reductase inhibitors (statins) has shown contradictory results in pre-clinical and clinical models. In some experimental models and in some but not all human studies, this therapy reduces the biliary cholesterol content and the lithogenicity index; however it has not been demonstrated to be useful in the dissolution of cholesterol gallstones in prospective clinical studies (Chapman et al., 1998; Hillebrant et el., 2002; Porsch-Ozcurumez et al., 2001).

The main problem is that nowadays there is no form for efficient primary prevention of gallstone disease in the general population or in specific high-risk groups (women, third trimester of pregnancy, puerperium, overweight or obese women, programmed weight loss in the morbidly obese, gastroplasty and intestinal by-pass in the morbidly obese, prolonged fasting, prolonged enteral nutritional therapy); nor there are effective medical therapies (e.g. dissolution of already formed gallstones).

It is known that the 2-azetidinones and their respective pharmacological families are used in the treatment of elevated plasma cholesterol and are protected by diverse patents. For example, the documents U.S. Pat. No. 5,631,365, WO 2004 010948, WO 2004 081002, WO 2004 000803, WO 2004 000804, WO 2004 000805, divulge the use of Ezetimibe for the treatment of cholesterol disorders such as hypercholesterolemia, atherosclerosis, or cholesterol induced tumors.

Even though cholelithiasis is a disease of cholesterol metabolism, there is not a clear correlation between total cholesterol plasma levels, LDL cholesterol plasma levels or atherosclerosis with the presence of cholesterol gallstones or with a higher risk of developing cholelithiasis. Consequently, the different therapies developed for the treatment of hypercholesterolemia or dyslipidemias, main risk factors of atherosclerotic cardiovascular illness, have not been demonstrated to be effective in the treatment and/or prevention of cholesterol gallstone disease. Only hypertriglyceridemia and low plasma levels of HDL cholesterol have been associated in some studies with a higher risk of gallstone disease, without demonstrating a causal relationship between these serological variables and the development of cholelithiasis (Paigen, 2002).

Because of the arguments presented above is that the present invention will solve a problem with the technique, since it is not an obvious inference that the current techniques developed for the treatment of plasma dyslipidemias and/or atherosclerosis are effective in the treatment of gallstone disease.

A 2-azetidinone compound in combination with other drugs and its use in the treatment of cholesterol gallstone disease or cholelithiasis is mentioned in the documents WO2004001002 and WO20030153541. These documents specifically proclaim a pharmaceutical composite that includes a moderator of a LXR receptor and an agent of lipidic regulation such as Ezetimibe. The orphan nuclear receptor LXR acts a transcriptional regulator of genes involved in cholesterol metabolism and trafficking. When it binds endogenous ligands (oxysterols) or synthetic ligands it inhibits cholesterol synthesis (specially in the liver) and at the same time stimulates cholesterol catabolism into bile salts and cholesterol exit into the bile in rodents (Yu et al., 2003). It was demonstrate in experimental animal models (rodents) that the activation of this nuclear receptor lowers cholesterol plasma levels, particularly under cholesterol rich experimental diets that increase cholesterol content in mice bile by activating specific genes known as ABCG5 and ABCG8. This findings have not been demonstrated in humans yet since there are no drugs approved for human use. The available evidence from experimental animals suggest that the use of LXR activating drugs could also increase the risk of cholesterol gallstone formation in the biliary tree since the stimulation of LXR increases cholesterol content in the bile (Yu et al., 2003). There is no evidence in the literature showing that the use of LXR synthetic ligands (pharmacological), alone or in combination with Ezetimibe, inhibit the formation of cholesterol stones of the biliary tree.

The document WO2005 00217 divulges a compound that combines an anti-obesity agent and an anti-dyslipidemiant agent, among which there is an inhibitor of cholesterol absorption like Ezetimibe. This composite is indicated for its use in dyslipidemia-related disorders. The document WO2004078716 describes piperazine derivatives and their use as agonists of the melanochortin receptor (MC-R), indicated for the treatment of obesity. Additionally, document WO2004030637 discloses the use of modulators of the metabotropic glutamate receptor 5 (mGluR5) in the treatment of obesity related disorders. In the description they mention that "anti-obesity agents apt to be used in combination with a modulator of the mGluR5 include, among other cholesterol lowering agents, cholesterol absorption inhibitors such as 2-azetidinones like Ezetimibe". Document WO2004031175 describes compounds that act as agonists of NPY receptors, specifically NPY Y5 receptors. This compounds are useful for the treatment of diverse ailments related to NPY, being among them gallbladder disease. Obesity and associated medical problems such as gallstone disease can also be treated. Ezetimibe is mentioned as an example of other active ingredients that can be administered in combination with the compound related to the invention.

Overweight (body mass index, BMI, >25 kg/mt$^2$) and obesity (BMI>28) are established risk factors for developing cholelithiasis mainly in women, being this evidence more clear than in men. Overweight and obesity increase the risk of cholelithiasis 2-3 times in women but not in men. On the other hand, abrupt weight loss (>1.5 kg/week) in the morbidly obese (BMI>35), either by hypocaloric dietary treatment (approximately 1,000 kcal/day) or though bariatric surgery, increases the risk of developing cholelithiasis, and it has been reported that 20-40% of these patients can develop cholelithiasis in the subsequent weeks or months. It is not clear why only some overweight or obese subjects develop cholelithiasis (20-30% according to some studies), and other environmental and/or genetic factors that may determine this susceptibility have been suggested (Paigen, 2002 and references therein).

Nevertheless, most of the people that develop cholelithiasis are not overweight or obese and therefore this association is far from being universal. It is probable that the treatment of obesity per se with the current techniques could even increase the risk of developing cholelithiasis in these subjects. On the other hand the prevention of this metabolic condition could lower, at least in part, the frequency of this disease in high risk populations (genetically susceptible).

Because of the arguments presented above is that the present invention will solve a problem with the technique, since it is not obvious to infer that the current techniques developed for the treatment of morbid obesity and/or overweight are effective in the treatment of gallstones disease.

DETAILED DESCRIPTION OF THE INVENTION

Figure 1:
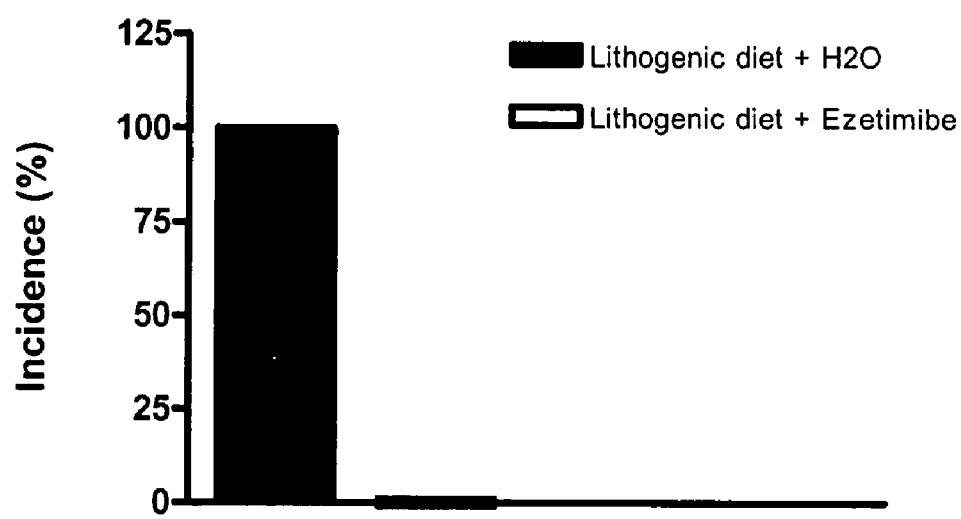
FIG. 1. The formation of cholesterol crystals and cholesterol gallstones is inhibited in C57BL/6 mice on lithogenic diet plus ezetimibe for 14 days.

This invention demonstrates that the use of specific inhibitors of cholesterol intestinal absorption that belong to the 2-AZETIDINONE class, specifically EZETIMIBE (SCH 58235), completely inhibits the development of cholelithiasis in a murine model of the disease on a lithogenic diet. This invention in a preclinical model of cholesterol gallstone disease allows to predict that the selective inhibition of cholesterol intestinal absorption is an effective therapeutic alternative in primary prevention and/or treatment of cholesterol gallstone disease in humans. In addition, as it was discussed in the Background section, it is possible to predict that that in humans, the combination of Ezetimibe (SCH 58235) with inhibitors of cholesterol hepatic neosynthesis (HMG-CoA reductase), could be more efficient than Ezetimibe (SCH 58235) alone in the prevention and/or treatment of gallstone disease.

EXAMPLE OF APPLICATION

Materials and Methods

Experimental Animal Disease Models. Spontaneous cholelithiasis is extremely rare in experimental or wild animals, probably because they secrete low levels of cholesterol into the bile and have therefore non-saturated cholesterol bile. However, different animal models (rabbit, hamster, prairie dog, squirrel and mouse) develop cholelithiasis similar to the human disease on cholesterol rich plus bile salts (cholic acid) and sometimes triglycerides rich experimental diets. The mouse is the best characterized experimental model where the development of the disease is dependent of a diet known as "lithogenic" (1.25% cholesterol, 0.5% cholic acid, 15% fat). Under these conditions most of the available mouse strains develop cholesterol cholelithiasis in variable proportions and times (Paigen, 2002). It has been established that there are strains more susceptible or more resistant to develop cholelithiasis, which could be genetically determined. The mice strains C57L and C57BL/6 are particularly susceptible to develop cholelithiasis (80-100% of the animals develop the disease in 2-4 weeks on lithogenic diet) (Paigen, 2002; Bouchard et al., unpublished data communicated in www.jax.org/pub-cgi/phenome). Studies performed in these models during the last years have been vital in the better understanding of the disease and for the discovery of genes that are potentially relevant in generating susceptibility to the illness (Paigen, 2002). In this preclinical innovation work we use the mouse strain C57BL/6.

We used mice C57BL/6J susceptible to the development of cholelithiasis originally obtained from Jackson Corp (Bar Harbor, Me., USA) and the colonies were grown in our Laboratory of Gastroenterology, Facultad de Medicina, P. Universidad Católica de Chile. The experimental groups were fed a control chow diet low in cholesterol (<0.02% cholesterol, Prolab RMH3000, PMI Feeds Inc., St. Louis, Mo.) or a lithogenic diet (1.25% cholesterol, 0.5% cholic acid, 15% fat, TD90221, Harlan Teklad, Madison, Wis.) (Amigo et al. 2000). These mice were also treated with Ezetimibe (Zetia®, Merk/Schering Plough) or placebo. In protocol #1 Zetia® tablets were grinded in a porcelain mortar and dissolved in water to be administered to the mice in one daily dose (08 h) of 5 mg/Kg weight by gavage in a final volume of 200 µw; the control groups were given the same volume of water by gavage without the drug. In protocol #2 Zetia® tablets were grinded in the same way described above, dissolved in 200 cc 100% ethanol (Merck) and added to the lithogenic diet previously grinded and dried for 48 h at room temperature. C57BL/6J mice received this lithogenic diet plus Zetia® in a estimated dose of 5-6 mg/kg/day during 30 days (the mice consume 4-5 gr of diet per day). The control group received the same grinded lithogenic diet, supplemented with 100% ethanol (200 cc) and dried for 48 h. During the study the mice were kept at constant room temperature, with day/night cycles of 09:00-21:00 h and 21:00-09:00 h respectively, and free access to food and water. Four groups of 8-10 week old male mice (5-10 per group) were place on the following experimental diets:

Protocol #1:
Group 1-A: Control chow diet plus water by gavage (n=10).
Group 1-B: Control chow diet plus Ezetimibe 5 mg/kg/day by gavage (n=10).
Group 2-A: Lithogenic diet plus water by gavage (n=10).
Group 2-B: Lithogenic diet plus Ezetimibe by gavage (n=10).
Protocol #2:
Group 1: Lithogenic diet for 30 days (n=5).
Group 2: Lithogenic diet plus Ezetimibe, 5-6 mg/kg/day for 30 days (n=5).

Surgery and sample harvest. The groups were maintained for 14 days (protocol #1) or 30 days (protocol #2) in the different experimental conditions. During the last three days of the protocols, 24 h depositions were collected from the different groups (pool) to determine the fecal excretion of neutral sterols (cholesterol) and acidic sterols (bile salts). At the end of the time established in the protocols, the mice were anesthetized (between 08:00-10:00 AM) with an intraperitoneal pentobarbital injection in doses of 4.5 mg per 100 gr body weight (Amigo et al., 2000) and subjected to surgery. Standardized surgery consists in an extended laparoscopy and visualization of abdominal organs, including liver, biliary tree and gallbladder. First, we performed a resection of the gallbladder (cholecystectomy), with the cystic duct previously ligated (Amigo et al., 2002; Amigo et al., 2000; Amigo et al., 2003b). The gallbladder is removed and visually inspected to determine the presence of gallstones. Then, the gallbladder bile is extracted to analyze the presence of cholesterol crystals in the fresh samples under the microscope with polarized light (20×). Aliquots are stored at −20° C. for subsequent chemical analysis. Afterwards, the common biliary duct is cannulated (biliary fistula) with a P-10 polyethylene cannula to collect bile during 15 minutes, determine bile flow by gravimetry (1 g bile=1 ml; bile flow is expressed as µl/min/g of mouse liver) and for posterior chemical analysis of biliary lipids and glutathione, as specified later. The inferior vena cava is punctured with an heparitinized tuberculine syringe to extract 500-800 ml of blood. Then, the liver is removed, weighted, frozen in liquid nitrogen and stored at −80 for subsequent analyses. The plasma is separated by centrifugation at 1,500 rpm and stored at −80° C. for later analysis. The animal protocols were approved by our institution Ethics Committee and the animals were treated according to international care rules for experimental animals.

Determination of lithiasis of the gallbladder and cholesterol crystals in gallbladder bile. The presence or absence of cholesterol gallstones in the mice gallbladder is determined by simple optic inspection, since the gallbladder is translucent and allows to easily detect the presence of particulate structures in its interior (gallstones or particulate sediments). In order to determine the presence of typical monohydrate cholesterol crystals, 10 µl of gallbladder bile are placed on a slide and analyzed by optic microscopy under polarized light with magnification of 10-20×. Cholesterol crystals are typically observed as birefringent crystals with the appearance of broken glass (Amigo et al., 2000; Miquel et al., 1998b; Moschetta, Bookout and Mangelsdorf, 2004).

Intestinal absorption of cholesterol and bile salts. The capacity of Ezetimibe to inhibit cholesterol and bile salt absorption was indirectly determined by quantification of neutral sterols (cholesterol) and acidic sterols (bile acids) present in the feces collected on day 12, 13 and 14 of the experiment (three days). In order to determine cholesterol (neutral sterols) fecal excretion, the feces were dried at 50° C. for three days and then weighted to obtain an average of fecal excretion per day (in grams). The feces were homogenized in a mortar, and 5 ml 2N NaOH:methanol, 1:1 are added per 100 mg (dry weight) aliquots of the homogenate. The sample is vortex and incubated at 60° C. for 1 h for saponification, then it is cooled and 5 ml petroleum ether is added followed by vigorous agitation to obtain the separation of the hydrophobic and hydrophilic phases. The samples are then centrifuged at 1,000 rpm for 10 minutes and the hydrophobic phase (upper layer) is recovered. Second and third extractions are performed by adding 5 ml petroleum ether to the hydrophilic phase. The hydrophobic phases are dried under gaseous nitrogen and the lipids are resuspended in 1 ml chloroform. 50 µl aliquots, in duplicate, are dried at room temperature, and total cholesterol is quantified according to the enzymatic method described above. The values obtained are expressed as µmoles cholesterol/day/100 g of mouse (Miettinen et al., 1965). In order to determine fecal excretion of bile acids the mice feces were collected during three days (days 12-14), dried at 50° C. for one week and weighted. The feces are then homogenized in a mortar; ($^{14}$C) cholic acid, 200,000 cpm is added to 1 g of the homogenate to determine the degree of recovery. The samples are then mixed with NaBr, NaOH and HCl, dissolved in ethanol and incubated at 120° C. for 8 h in a reflux system. The hydrolyzed fecal samples are resuspended in NaOH and dried under gaseous $N_2$. The pellet obtained is resuspended in ethanol and run through Sep-Pak columns to eliminate all bile salts contaminants. The bile salts are eluted with a solution methanol:water 85:15 and dried under gaseous $N_2$. The samples are then resuspended in methanol, aliquots taken in duplicate and bile salts measured using hydroxysteroid dehydrogenase just as they are measured in the bile. The value obtained is normalized with the $^{14}$C cholic acid recovery (Mendez-Sanchez et al., 1998). Determination of plasma cholesterol, biliary lipids and biliary glutathione. The plasma cholesterol content and the cholesterol, bile salts and phospholipid content in the gallbladder and hepatic bile are determined by enzymatic methods. Biliary cholesterol concentration: 500 µl buffer (Tris-HCl pH 7.6, phenol, chlorophenol, Triton X-100, sodium collate, aminoantipyrine, and the enzymes cholesterol esterase, cholesterol oxidase and peroxidase) are added to 5 µl hepatic bile or 1 µl gallbladder bile. This reaction mix is incubated for 10 minutes at 37° C. and the absorbance quantified at 500 nm.

The values obtained are interpolated in a standard cholesterol concentration curve. Plasma cholesterol is quantified in the same way from 5 µl plasma (Abell et al., 1974). Bile salts concentration is determined by adding 1 ml buffer (potassium phosphate pH 8.0, hydrazine hydrate, NAD and hydroxysteroid dehydrogenase) to 2 µl hepatic bile or 1 µl gallbladder bile. This reaction mix is incubated at 30° C. for 30 minutes and the absorbance quantified at 340 nm. The values obtained are interpolated in a standard Taurocholate concentration curve (Talalay, 1960). Phosphatidylcholine (phospholipids) in the bile is determined by adding 1 ml buffer (Tris-HCl pH 7.6, phenol, aminoantipyrine, Triton X-100, $CaCl_2$, phopholipase D, choline oxidase and peroxidase) to 5 µl hepatic bile or 1 µl gallbladder bile. The reaction mix is incubated at 37° C. for 10 minutes and the absorbance measured at 500 nm. The values obtained are interpolated in a standard phosphatidylcholine concentration curve (Gurantz et al., 1981).

Determination of biliary lipids debit. In all the cases presented above, the concentration value in mM is given in terms of debit, indicating the amount of each class of lipid secreted into the bile per time unit in relation to liver or mouse weight. The debit calculation is performed by multiplying the concentration value of each lipid by bile flow.

Biliary gluthation. Biliary gluthation was quantified from the bile obtained by cannulation of the biliary duct for a 5 minute period with tubes containing 5 µl sulfosalicylic acid. Duplicate samples were taken from these samples and diluted 1:60 in sulfosalicylic acid. The enzymatic reaction for measuring glutathione was done by adding buffer (sodium phosphate, EDTA, DNTB, NADPH) and the enzyme GSH reductase. The reaction mix was incubated at 37° C., measured at 412 nm, and an enzymatic kinetic curve was obtained using different GST concentrations as standard. The enzymatic activity was transformed into glutathione concentration present in the bile. Once the concentration of biliary gluthation was determined, we obtained glutathione debit as it was described earlier for biliary lipids (Anderson, 1985).

Determination of the cholesterol saturation index in gallbladder bile samples. This index was obtained using each biliary lipid concentration (cholesterol, bile salts and phosphatidylcholine). From these concentrations we established the total amount of lipids, the phospholipids/(bile salt phospholipids) and the molar cholesterol percentage. With this data and a table to calculate the saturation index we were able to determine the cholesterol saturation index as it was previously described (Carey, 1978).

Plasma lipoprotein profile. In order to characterize the plasma lipoprotein profile we collected 40 µl of serum from 5 mice in each group (200 µl pool for each experimental group). The samples were loaded into a sepharose 6B column (Fast Pressure Liquid Chromatography, FPLC, Pharmacia) were the lipoproteins are separated according to their weight. The column is eluted and fractions collected (37 fractions, 300 µl each). For each fraction the cholesterol content is calculated, which allowed us to establish the distribution of the big (VLDL, IDL/LDL) and small lipoproteins (HDL) as follows. To each fraction collected we added 200 µl of the reaction mix for measuring total cholesterol (without diluting with water). The enzymatic reaction was done exactly as described for biliary cholesterol. The value obtained for each fraction is given as µg cholesterol per fraction.

Determination of hepatic cholesterol. The hepatic cholesterol content is quantified from hepatic tissue (50 mg) that is homogenized in chloroform/methanol 2:1. The homogenate is incubated at 50° C. for 30 minutes, and then distilled $H_2O$ is added to separate the phases. The mix is vortexed and incubated at 4° C. for two hours and centrifuged at 1,000 rpm for 20 minutes. The lower phase (hydrophobic-chloroform) is removed and dried under gaseous nitrogen. The lipids on the tube wall are resuspended in chloroform plus Triton X-100 0.5% v/v. Four aliquots are taken and dried at room temperature. Total cholesterol content was measured to half of the tubes by the enzymatic method described earlier for biliary cholesterol. To the other half, free cholesterol was measured in buffer (Tris-HCl pH 7.6, Triton X-100, 0.2% phenol, aminoantipyrine) plus the enzymes cholesterol oxidase and peroxidase. The samples are incubated and quantified in the same way described for total cholesterol. The cholesterol ester content for each sample is calculated as the difference between total cholesterol and free cholesterol. The values obtained in each case are given as mg cholesterol/g liver (Folch et al., 1957).

Expression of Specific Bile Salts (Ntcp, Bsep), Phospholipid (MDR2) and Organic Anions or Glutathione (MRP2); And Determination of Glutathione Synthesis (Gluthamylcystein-Synthetase (GGCS)).

Western Blot analysis. We evaluated protein expression levels of the bile salts transporters Ntcp (sinusoidal pole) and Bsep (cannicular pole) by Western blotting in total liver membranes or liver plasma membranes from mice treated with the different diets. Total membranes were obtained from liver fragments homogenized in Tris-HCl pH 7.5, $MgCl_2$ and sucrose. The homogenates were centrifuged at 1,000 g to separate nuclei, and the supernatants were then centrifuged at 100,000 g. The pellet, containing the total membranes, was resuspended in the buffer described above and proteins were quantified by the Bradford method. Aliquots containing 50 µg protein were separated by SDS-PAGE and transfer to nitrocellulose. The membranes were incubated in buffer TBS-T (Tris-HCl pH 7.5, NaCl and Tween-20), milk 5% w/v plus the antibodies to evaluate the different proteins (Bsep, Ntcp). The secondary antibodies were IgG anti rabbit or anti mouse coupled to peroxidase. The protein signals were detected by the ECL method. As internal loading control we used beta-actin, a protein with constitutive expression that does not change its expression levels with the diets and drugs used.

Northern Blot Analysis.

Figure 8:
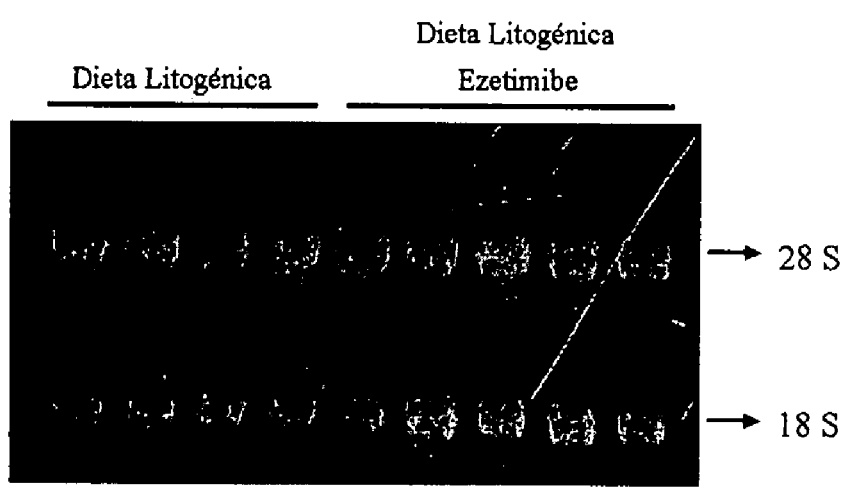
FIG. 8. Integrity of the RNA isolated from mice on a lithogenic diet with and without Ezetimibe.

Total RNA extraction. 80 mg hepatic tissue frozen at –70° C. was homogenized in 800 µl solution D, following the method described by Chomczynski and Sacchi, 1987. The RNA concentration was calculated by measuring the absorbance at 260 nm and its purity by the ratio $OD_{260}/OD_{280}$. The samples are stored at –20° C. RNA electrophoresis. 10 µg of total RNA are dried under gaseous $N_2$ or vacuum for 10 minutes. 10 µl loading buffer were added, and the samples heated to 65° C., loaded into a denaturing 1% agarose/formaldehyde gel and run at 100 volts for 4 hours. The RNA integrity was determined by the clear visualization of the 28 S and 18 S ribosomal RNAs (FIG. 8).

Northern Blot and hybridization with radioactive probes. The gel with the RNA samples is washed with DEPC $H_2O$ for 10 minutes to eliminate formaldehyde and then incubated for 20 minutes with 50 mM NaOH for partial RNA hydrolysis. After a 10 minute wash with DEPC $H_2O$ to eliminate NaOH, the samples are transferred from the gel to Nylon membranes (Hybond-N, Amersham Pharmacia) over night by a capillary system. After the transfer, the RNA is fixed to the membrane by heating at 80° C. for 2 h.

Probe labeling by "de novo synthesis". For the radioactive labeling of probes specific for MDR2, MRP2 and gamma-gluthamylcystein-synthetase (G-GCS), we used the Prime-a-gene Labeling System, Promega, based on the method developed by Feiberg and Vogelstein, 1983. We used a fragment of the gene of interest (generated by PCR), dCTP-a-$P^{32}$, a mix of unlabeled nucleotides and Klenow fragment for the probe labeling. The percentage of incorporated radioactivity into the probe was always over 60%.

Membrane hybridization with the labeled probe. The probe was denatured at 100° C. for 5 minutes and incubated with the pre-hybridized membrane at 65° C. over night. After 2 washes, the membrane was subjected to autoradiography.

Statistical analysis. The results are presented as mean±standard deviation. Statistical significance among the groups treated with Ezetimibe and controls was determined by the non-paired Student T test. A value of p<0.05 was considered significant.

Protocol #1 Results
Lithiasis of the Gallbladder.

100% of the mice that received a lithogenic diet and water by gavage for 14 days developed gallstones and presented cholesterol monohydrate crystals in the gallbladder bile. In contrast, none of the mice that received a lithogenic diet plus Ezetimibe by gavage for 14 days developed gallstones or cholesterol crystals in the gallbladder (FIG. 1). As it was expected, the mice on a control diet low in cholesterol, either with water or Ezetimibe, did not develop cholelithiasis or cholesterol crystals in the bile. This is the crucial result that supports the present invention, the complete inhibition in the generation of cholelithiasis in a preclinical experimental model through the use of Ezetimibe, a potent selective blocker of cholesterol intestinal absorption belonging to the 2-azetinedione family.

Body and Liver Weight

No significant difference was found in the animals' weight, liver weight and liver/body weight index between the mice on control diet with or without Ezetimibe. On lithogenic diet, a significantly increase in liver weight was observed. This increment in liver weight is not significantly different between mice that had not been treated with Ezetimibe and those that had been treated (Table 1).

Cholesterol and Plasma Lipoproteins

Figure 2:
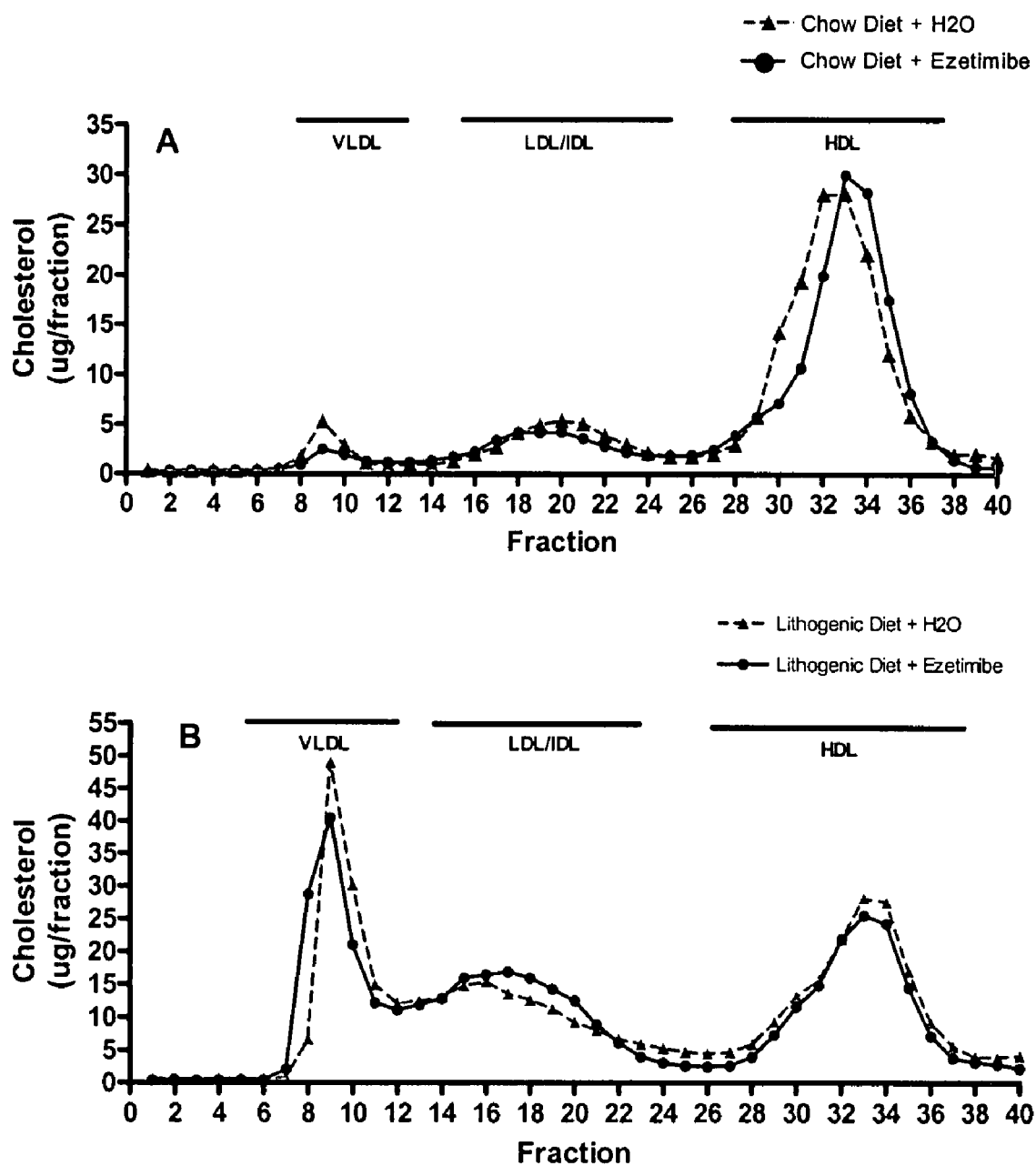
FIG. 2. (A) Plasma lipoprotein profile in C57/BL6 mice after 14 days on Chow diet with and without Ezetimibe. VLDL, very low density lipoproteins; LDL, low density lipoproteins; IDL, intermediate density lipoproteins; HDL, high density lipoproteins. (B) Plasma lipoprotein profile in C57/BL6 mice after 14 days on lithogenic diet with and without Ezetimibe. VLDL, very low density lipoproteins; LDL, low density lipoproteins; IDL, intermediate density lipoproteins; HDL, high density lipoproteins.

The concentration of total cholesterol in plasma was similar between the group of mice on the control diet with or without ezetimibe. The concentration of plasma cholesterol increases on a lithogenic diet for 14 similarly in the groups with or without ezetimibe. (Table 1). This result is in contrast with other researchers finding where they saw significant differences between mice and high cholesterol diet with and without ezetimibe. However, the mentioned experiments were performed for longer treatment periods (longer than two months), what may explain our results. The plasma lipoprotein profile between the experimental groups that received ezetimibe and the controls did not show significant differences (FIG. 2).

Cholesterol Fecal Excretion and Hepatic Cholesterol Content

In order to verify the inhibitory effect of Ezetimibe on cholesterol absorption on the control and lithogenic diets used, we quantified hepatic cholesterol content and cholesterol fecal excretion (neutral sterols). The fecal excretion of neutral sterols in 24 h, on days 13-14 of experimentation was 5.36 μmol per day per 100 g mouse on control diet without Ezetimibe; and 19.98 μmol per day per 100 g mouse on control diet plus Ezetimibe (37% increment), in accord with previous studies on similar low cholesterol diets. On lithogenic diets, the fecal excretion of neutral sterols (cholesterol) increases significantly in both groups (8 times), being 55% higher in the mice that received Ezetimibe compared with those that were not treated with Ezetimibe (Table 2).

TABLE 2

| Diet | Fecal excretion of neutral sterols (μmol/day/100 g mouse) | Fecal excretion of bile acids (μmol/day/100 g mouse) |
|---|---|---|
| Chow | 5.36 | 72.97 |
| Chow + Ezetimibe | 19.98 | 55.42 |
| Lithogenic | 106.73 | 957.00 |
| Lithogenic + Ezetimibe | 165.79 | 909.20 |

The hepatic cholesterol content in mice on control diet was similar between those that received water or Ezetimibe, being rather smaller (20%) in the latter. Total cholesterol content increased significantly in the mice on lithogenic diet (360%), however, this increment is significantly smaller in the mice on lithogenic diet plus Ezetimibe (38%) (Table 1). The increase in hepatic cholesterol corresponds to an increase in both cholesterol ester and free cholesterol, being more relevant the esterified cholesterol increase in the mice without Ezetimibe. These results confirm that dietary cholesterol that accumulates in the liver on a lithogenic diet is drastically reduced by Ezetimibe. Ezetimibe does not significantly affect fecal excretion of bile salts (Table 2), both on control and lithogenic diets, in agreement with previous studies that demonstrate Ezetimibe selectivity in the inhibition of cholesterol intestinal absorption.

Lipid Content and Cholesterol Saturation Index in Gallbladder Bile

On the control diet, Ezetimibe did not induce significant changes in cholesterol content, bile salts or lecitine in the mice gallbladder bile; the cholesterol saturation index was also similar in both groups (Table 3).

TABLE 1

| Diet | Liver Weight (mg) | Plasma Cholesterol (mg/dl) | Hepatic Cholesterol (mg/ml) | | |
|---|---|---|---|---|---|
| | | | Total | Free | Esterified |
| Chow | 1.24 ± 0.06 | 80.65 ± 5.4 | 2.82 ± 0.32 | 2.50 ± 0.22 | 0.31 ± 0.22 |
| Chow + Ezetimibe | 1.17 ± 0.09 | 86.21 ± 13.8 | 2.26 ± 0.59 | 1.91 ± 0.65 | 0.34 ± 0.16 |
| Lithogenic | 1.56 ± 0.09* | 193.68 ± 30.63* | 10.07 ± 2.62* | 3.61 ± 1.05* | 6.66 ± 2.23* |
| Lithogenic + Ezetimibe | 1.45 ± 0.13* | 161.38 ± 38.96* | 3.91 ± 1.05*& | 2.59 ± 0.24 | 1.31 ± 0.99& |

*p < 0.05 compared with its respective control group;
&p < 0.05 compared with the group on lithogenic diet without Ezetimibe.

TABLE 3

| Diet | Gallbladder Bile | | | |
|---|---|---|---|---|
| | Cholesterol (mmol/L) | Bile salts (mmol/L) | Phospholipids (mmol/L) | Colesterol Saturation Index (%) |
| Chow | 1.14 | 60.16 | 12.00 | 51.3 |
| Chow + Ezetimibe | 1.19 | 65.00 | 11.62 | 51.7 |
| Lithogenic | 4.10 | 77.89 | 14.21 | 136.2 |
| Lithogenic + Ezetimibe | 1.35 | 70.37 | 12.92 | 53.2 |

As it is already known, the lithogenic diet per se triggers a significant increase in cholesterol content in the gallbladder bile (4-5 times), without causing significant changes in bile salts or lecitine; therefore, the cholesterol saturation index is also increased significantly (2-3 times). The treatment with Ezetimibe on a lithogenic diet notoriously decreases cholesterol content in the gallbladder bile (50-60%), with a concomitant reduction in the cholesterol saturation index (50%). In fact, the cholesterol saturation index and cholesterol content values in the gallbladder bile of mice on lithogenic diet plus Ezetimibe, were similar to those obtained by other researchers using murine models with low and high cholesterol diets with and without Ezetimibe (but in the absence of cholic acid and fat) (Repa et al, 2002).

Biliary Flow and Hepatic Secretion of Lipids and Glutathione

Figure 3:
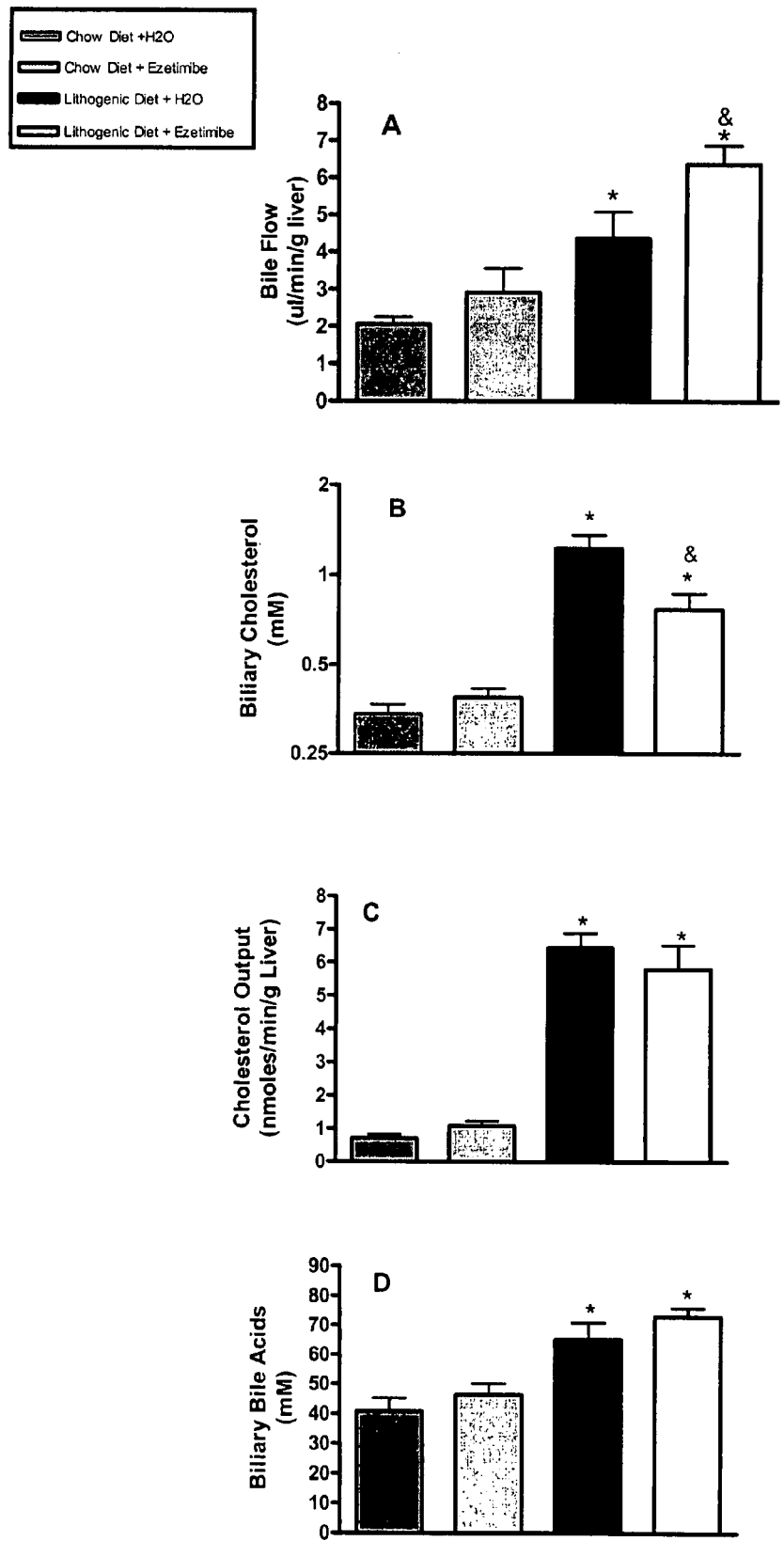
FIG. 3. (A) Bile flow in C57BL/6 mice that received Chow or lithogenic diets with or without Ezetimibe. (B) Bile cholesterol concentration in mice on the diets mentioned above. (C) Biliary Cholesterol secretion. (D) Bile acids concentration in the bile. (E) Biliary bile acids secretion. (F) Phospholipid concentration in the bile. (G) Biliary phospholipids secretion. *, p<0.05 respect to its control group; &, p<0.05 respect to the group on lithogenic diet without Ezetimibe.
Figure 4:
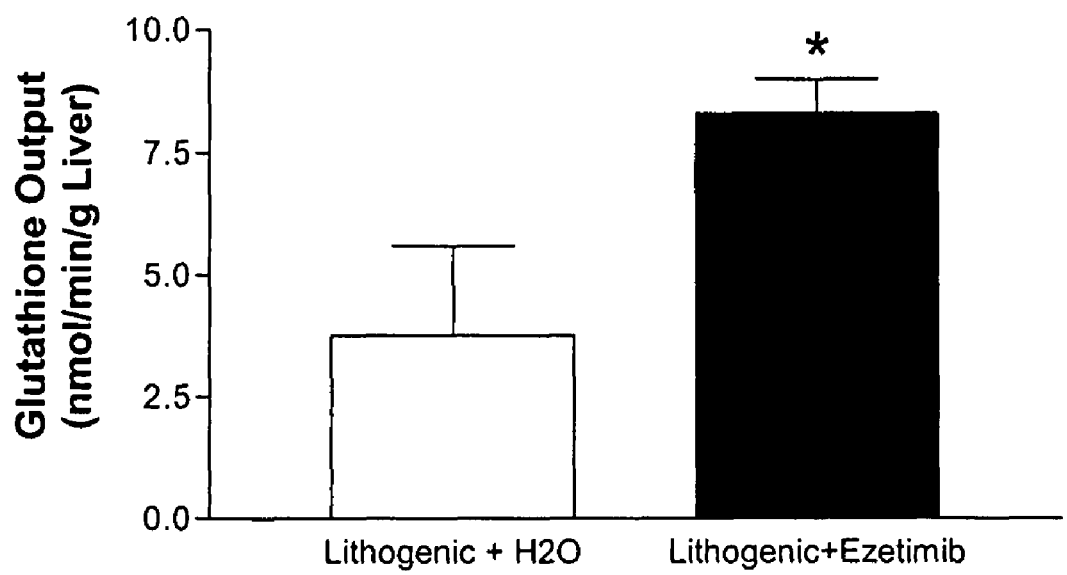
FIG. 4. Glutathione biliary secretion in C57BL/6 mice on a lithogenic diet with and without Ezetimibe. *,p<0.05 respect to a group on a lithogenic diet plus water.

The biliary flow and hepatic secretion of lipids was also established in the four experimental groups, representing additional original observations that are part of our invention. On low cholesterol control diet, ezetimibe produces a slight non-significant increase in biliary flow (30-40%) (FIG. 4). As it is already known, a lithogenic diet per se significantly increases the biliary flow (200-300%), as well as increasing biliary lipid secretion, bile salts, lecitine, and cholesterol (FIG. 3). Surprisingly, ezetimibe treatment on lithogenic diet triggered an even greater increment in biliary flow, significantly higher to that of the group lithogenic diet without ezetimibe (50-60% larger). We noticed that this larger increment in biliary flow, was associated to an increase in the secretion of bile salts and phospholipids (dependent on bile salts secretion), but did not associate to a greater secretion of biliary cholesterol compared to the group that did not receive ezetimibe (FIG. 3). Since biliary flow is mainly dependent on hepatic secretion of bile salts but also on the biliary secretion of other solutes such a glutathione; we quantified glutathione biliary secretion in the mice on lithogenic diet with or without ezetimibe. We observed a significant increase in glutathione secretion (200%) in the mice treatment with ezetimibe compared with those that received only the lithogenic diet (FIG. 4). These results suggest that, on a lithogenic diet, ezetimibe increases biliary flow by mechanism dependent and independent (glutathione) of bile salts, which could be relevant as additional mechanisms that favor cholelithiasis inhibition in this preclinical model.

Hepatic Expression of Proteins or their mRNAs Involved in the Transport of Cholesterol, Bile Salts and Glucuronized Xenobiotics.

In order to establish if the differences observed in the biliary flow and in the secretion of biliary lipids and glutathione between the group of mice treated with lithogenic diet and the group on lithogenic diet plus Ezetimibe for 14 days could be explained by changes in the hepatic expression of transporters specific for these solutes (phospholipids, bile salts and organic anions), we determined their expression levels by western blotting and/or northern blotting. There were no significant differences between the groups in the hepatic expression of SR-BI, Ntcp, Bsep, MRP2 and GGCS. There was only a slight but statistically significant decrease in the phospholipid transporter MDR2 at the mRNA level. However, there was no concomitant decrease in mdr2 protein levels (data not shown) or a higher biliary secretion of phospholipids in mice on lithogenic diet plus Ezetimibe. Therefore, we propose that the increase in biliary flow and in the secretion of bile salts, phospholipids and glutathione in mice on lithogenic diet plus Ezetimibe compared to those on lithogenic diet without Ezetimibe, is not the result of changes in the expression of specific transporters. These changes could be explained by the subtractive effect of Ezetimibe on the liver cholesterol content. It is hypothesized that livers with lower cholesterol content (cholesterol depleted) have a larger capacity to transport solutes such as bile salts, lecitine and glutathione than cholesterol overcharged livers. This is an innovative point of view and allows to suggest that Ezetimibe could have a protective effect against endogenous (cholestasis, fatty acids) or exogenous (some organic anions) xenobiotics.

Results Protocol #2

Figure 5:
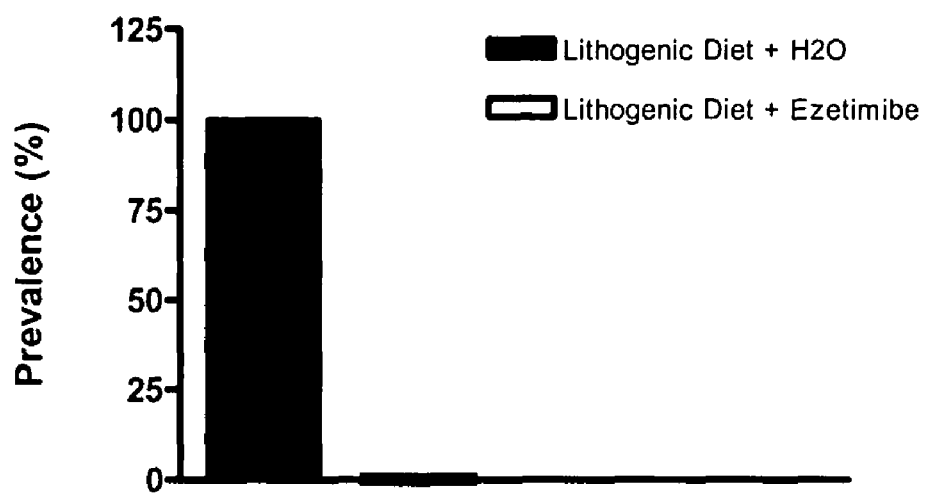
FIG. 5. Ezetimibe inhibits the formation of cholesterol crystals and cholesterol gallstones in C57BL/6 mice on a lithogenic diet for 30 days.
Figure 6:
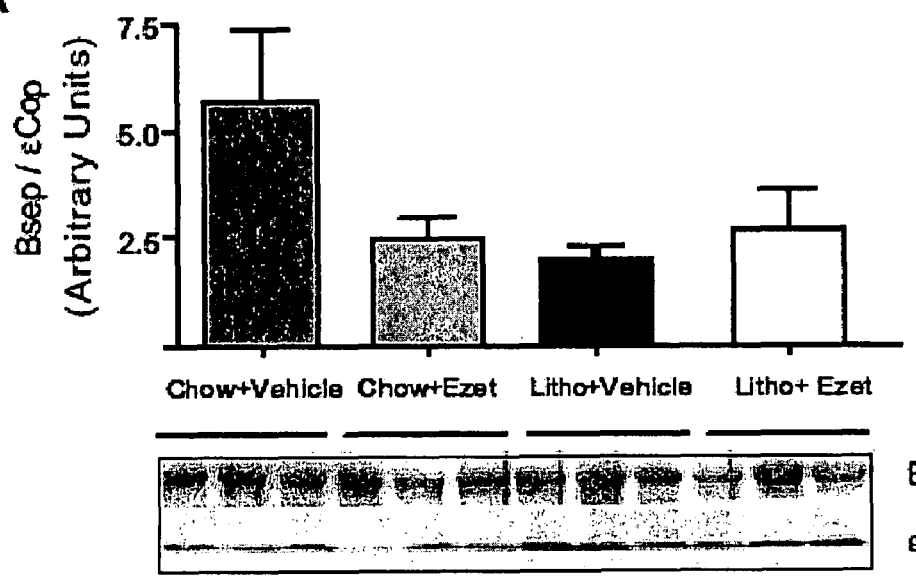
FIG. 6. Hepatic protein expression levels of the critical bile salts transporters, Bsep (A) and Ntcp (B) in mice on control and on lithogenic diets, with or without Ezetimibe. Bsep does not show significant changes with Ezetimibe on both diets. Ntcp shows a lower expression level on a lithogenic diet, but this decrease is significantly attenuated with Ezetimibe. *, p<0.05 respect a chow diet control; &, p<0.05 respect to a lithogenic diet plus water.
Figure 6:
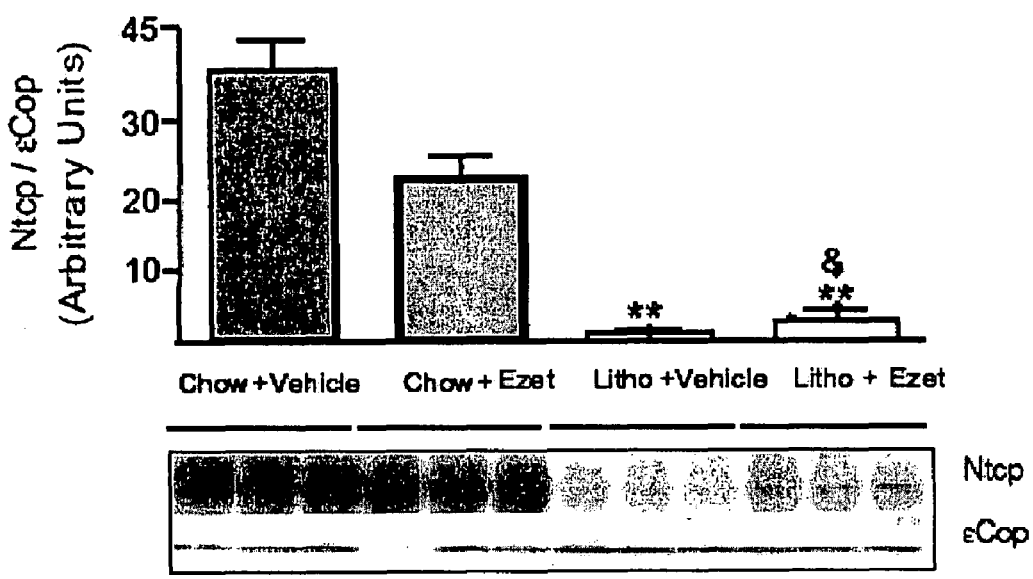
Figure 7:
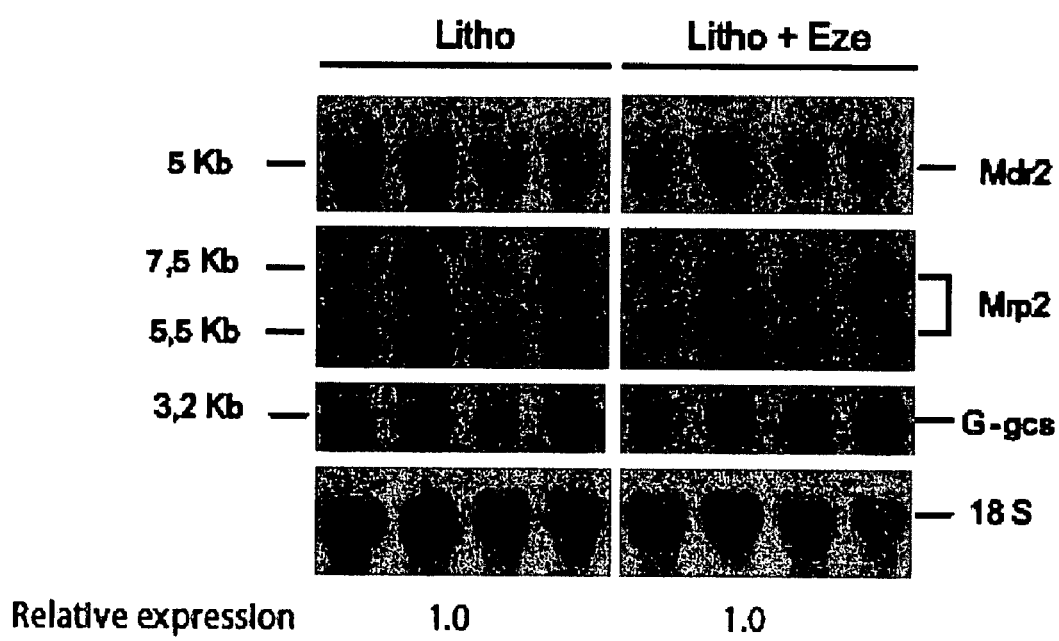
FIG. 7. mRNA expression levels of MDR2, MRP and G-GCS in the liver of mice on a lithogenic diet with or without Ezetimibe. Quantification of the radioactive specific bands from the Northen analysis shown as relative units to 18S. (B) Northern analysis showing that only the phospholipid transporter MDR2, has a small but statistically significant decrease.

Since Ezetimibe inhibited the formation of gallstones in the 2 week protocol (14 days), we wanted to establish if its effect was maintained for longer diet periods. Therefore, we supplied Ezetimibe directly in the lithogenic diet (no by gavage) during twice the time period (30 days). Again, the use of Ezetimibe completely inhibited the formation of cholesterol gallstones (FIG. 5). As it was expected, 100% of the mice on lithogenic diet developed cholelithiasis; in contrast, no animals (0%) under the same diet plus Ezetimibe developed gallstones or cholesterol crystals in the gallbladder. This last result demonstrates categorically the potent and prolonged protective effect of Ezetimibe on the development of cholelithiasis in a murine model.

References

Accatino, L., Pizarro, M., Solis, N., Arrese, M., Koenig, C. S. 2003. Bile secretory function after warm hepatic ischemia-reperfusion injury in the rat. *Liver Transpl* 9:1199-210

Amigo, L., Mardones, P., Ferrada, C., Zanlungo, S., Nervi, F., Miquel, J. F., Rigotti, A. 2003a. Biliary lipid secretion, bile acid metabolism, and gallstone formation are not impaired in hepatic lipase-deficient mice. *Hepatology* 38:726-34

Amigo, L., Mendoza, H., Castro, J., Quinones, V., Miquel, J. F., Zanlungo, S. 2002. Relevance of Niemann-Pick type C1 protein expression in controlling plasma cholesterol and biliary lipid secretion in mice. *Hepatology* 36:819-28

Amigo, L., Quinones, V., Mardones, P., Zanlungo, S., Miquel, J. F., Nervi, F., Rigotti, A. 2000. Impaired biliary cholesterol secretion and decreased gallstone formation in apolipoprotein E-deficient mice fed a high-cholesterol diet. *Gastroenterology* 118:772-9

Amigo, L., Zanlungo, S., Mendoza, H., Miquel, J. F., Nervi, F. 1999. Risk factors and pathogenesis of cholesterol gallstones: state of the art. *Eur Rev Med Pharmacol Sci* 3:241-6

Amigo, L., Zanlungo, S., Miquel, J. F., Glick, J. M., Hyogo, H., Cohen, D. E., Rigotti, A., Nervi, F. 2003b. Hepatic overexpression of sterol carrier protein-2 inhibits VLDL production and reciprocally enhances biliary lipid secretion. *J Lipid Res* 44:399-407

Apstein, M. D., Carey, M. C. 1996. Pathogenesis of cholesterol gallstones: a parsimonious hypothesis. *Eur J Clin Invest* 26:343-52

Bilhartz, L. E. 1988. Cholesterol gallstone disease: the current status of nonsurgical therapy. *Am J Med Sci* 296:45-56

Bosner, M. S., Ostlund, R. E., Jr., Osofisan, O., Grosklos, J., Fritschle, C., Lange, L. G. 1993. Assessment of percent cholesterol absorption in humans with stable isotopes. *J Lipid Res* 34:1047-53

Carey, M. C. 1993. Pathogenesis of gallstones. *Am J Surg* 165:410-9

Carey, M. C., Paigen, B. 2002. Epidemiology of the American Indians' burden and its likely genetic origins. *Hepatology* 36:781-91

Carr, T. P., Andresen, C. J., Rudel, L. L. 1993. Enzymatic determination of triglyceride, free cholesterol, and total cholesterol in tissue lipid extracts. *Clin Biochem* 26:39-42

Chapman, B. A., Burt, M. J., Chisholm, R. J., Allan, R. B., Yeo, K. H., Ross, A. G. 1998. Dissolution of gallstones with simvastatin, an HMG CoA reductase inhibitor. *Dig Dis Sci* 43:349-53

Cheng, A. Y., Leiter, L. A. 2003. Clinical use of ezetimibe. *Can J Clin Pharmacol* 10 Suppl A:21A-5A Cooper, A. D. 1991. Metabolic basis of cholesterol gallstone disease. *Gastroenterol Clin North Am* 20:21-46

Csendes, A., Korn, O., Medina, E., Becerra, M., Csendes, P. 1993. [Biliary surgery mortality in Chile in 1990. Cooperative study in 17 hospitals]. *Rev Med Chil* 121:937-42

Davidson, M. H. 2003. Ezetimibe: a novel option for lowering cholesterol. *Expert Rev Cardiovasc Ther* 1:11-21

Davis, H. R., Jr., Compton, D. S., Hoos, L., Tetzloff, G. 2001. Ezetimibe, a potent cholesterol absorption inhibitor, inhibits the development of atherosclerosis in ApoE knockout mice. *Arterioscler Thromb Vasc Biol* 21:2032-8

Dietschy, J. M., Turley, S. D., Spady, D. K. 1993. Role of liver in the maintenance of cholesterol and low density lipoprotein homeostasis in different animal species, including humans. *J Lipid Res* 34:1637-59

Everhart, J. E. 1994. Gallstones. In: Digestive Diseases in the United States: Epidemiology and Impact. J. E. Everhart, editor. pp. 647-692. US Department of Health and Human Services, PHS NIDDK, US Government Printing Office, Washington D.C.

Everhart, J. E., Khare, M., Hill, M., Maurer, K. R. 1999. Prevalence and ethnic differences in gallbladder disease in the United States. *Gastroenterology* 117:632-9

Everhart, J. E., Yeh, F., Lee, E. T., Hill, M. C., Fabsitz, R., Howard, B. V., Welty, T. K. 2002. Prevalence of gallbladder disease in American Indian populations: findings from the Strong Heart Study. *Hepatology* 35:1507-12

Fielding, C. J., Fielding, P. E. 1995. Molecular physiology of reverse cholesterol transport. *J Lipid Res* 36:211-28

Gui, G. P., Cheruvu, C. V., West, N., Sivaniah, K., Fiennes, A. G. 1998. Is cholecystectomy effective treatment for symptomatic gallstones? Clinical outcome after long-term follow-up. *Ann R Coll Surg Engl* 80:25-32

Gylling, H., Miettinen, T. A. 2002a. Baseline intestinal absorption and synthesis of cholesterol regulate its response to hypolipidaemic treatments in coronary patients. *Atherosclerosis* 160:477-81

Gylling, H., Miettinen, T. A. 2002b. Inheritance of cholesterol metabolism of probands with high or low cholesterol absorption. *J Lipid Res* 43:1472-6

Hillebrant, C. G., Nyberg, B., Gustafsson, U., Sahlin, S., Bjorkhem, I., Rudling, M., Einarsson, C. 2002. Effects of combined treatment with pravastatin and ursodeoxycholic acid on hepatic cholesterol metabolism. *Eur J Clin Invest* 32:528-34

Holzbach, R. T. 1984. Animal models of cholesterol gallstone disease. *Hepatology* 4: 191S-198S Iglesias, P., Diez, J. J. 2003. New drugs for the treatment of hypercholesterolaemia. *Expert Opin Investig Drugs* 12:1777-89

Jeu, L., Cheng, J. W. 2003. Pharmacology and therapeutics of ezetimibe (SCH 58235), a cholesterol-absorption inhibitor. *Clin Ther* 25:2352-87

Johnston, D. E., Kaplan, M. M. 1993. Pathogenesis and treatment of gallstones. *N Engl J Med* 328:412-21

Jolley, C. D., Dietschy, J. M., Turley, S. D. 1999. Genetic differences in cholesterol absorption in 129/Sv and C57BL/6 mice: effect on cholesterol responsiveness. *Am J Physiol* 276:G1117-24

Kern, F., Jr. 1994. Effects of dietary cholesterol on cholesterol and bile acid homeostasis in patients with cholesterol gallstones. *J Clin Invest* 93:1186-94

Klett, E. L., Patel, S. B. 2004. Biomedicine. Will the real cholesterol transporter please stand up. *Science* 303:1149-50

Lipka, L. J. 2003. Ezetimibe: a first-in-class, novel cholesterol absorption inhibitor. *Cardiovasc Drug Rev* 21:293-312

Mason, E. E., Renquist, K. E. 2002. Gallbladder management in obesity surgery. *Obes Surg* 12:222-9

Mauricio Moreno, H. M., Ludwig Amigo, Silvana Zanlungo, Marco Arrese, Attilio Rigotti, Juan Francisco Miquel. 2003. Hepatic over-expression of caveolin increases bile salt secretion in mice. *Hepathology*, in review.

Medina, E., Pascual, J. P., Medina, R. 1983. [Incidence of biliary lithiasis in Chile]. *Rev Med Chil* 111:668-75

Miettinen, T. E., Kiviluoto, T., Taavitsainen, M., Vuoristo, M., Miettinen, T. A. 1998. Cholesterol metabolism and serum and biliary noncholesterol sterols in gallstone patients during simvastatin and ursodeoxycholic acid treatments. *Hepatology* 27:649-55

Miquel, J. F., Covarrubias, C., Villaroel, L., Mingrone, G., Greco, A. V., Puglielli, L., Carvallo, P., Marshall, G., Del Pino, G., Nervi, F. 1998a. Genetic epidemiology of cholesterol cholelithiasis among Chilean Hispanics, Amerindians, and Maoris. *Gastroenterology* 115:937-46

Miquel, J. F., Nunez, L., Amigo, L., Gonzalez, S., Raddatz, A., Rigotti, A., Nervi, F. 1998b. Cholesterol saturation, not proteins or cholecystitis, is critical for crystal formation in human gallbladder bile. *Gastroenterology* 114:1016-23

Moreno, M., Molina, H., Amigo, L., Zanlungo, S., Arrese, M., Rigotti, A., Miquel, J. F. 2003. Hepatic overexpression of caveolins increases bile salt secretion in mice. *Hepatology* 38:1477-88

Moschetta, A., Bookout, A. L., Mangelsdorf, D. J. 2004. Prevention of cholesterol gallstone disease by FXR agonists in a mouse model. *Nat Med* 10:1352-8

Nervi, F. 2001. [Cancer of the gallbladder in Chile]. *Rev Med Chil* 129:979-81

Paigen, B., Carey, M. C. 2002. Gallstones. In: Genetic basis of common diseases. R. A. King, Rotter, J. I., Motulsky, A. G., editor. pp. 298-335. Oxford University Press, New York Porsch-Ozcurumez, M., Hardt, P. D., Schnell-Kretschmer, H., von Bergmann, K., Darui, C., Nonhoff, J., Abletshauser, C., Klor, H. U. 2001. Effects of fluvastatin on biliary lipids in subjects with an elevated cholesterol saturation index. *Eur J Clin Pharmacol* 56:873-9

Repa, J. J., Dietschy, J. M., Turley, S. D. 2002. Inhibition of cholesterol absorption by SCH 58053 in the mouse is not mediated via changes in the expression of mRNA for ABCA1, ABCG5, or ABCG8 in the enterocyte. *J Lipid Res* 43:1864-74

Schwarz, M., Russell, D. W., Dietschy, J. M., Turley, S. D. 1998. Marked reduction in bile acid synthesis in cholesterol 7alpha-hydroxylase-deficient mice does not lead to diminished tissue cholesterol turnover or to hypercholesterolemia. *J Lipid Res* 39:1833-43

Stiehl, A., Raedsch, R., Rudolph, G., Walker, S. 1984. Effect of ursodeoxycholic acid on biliary bile acid and bile lipid composition in gallstone patients. *Hepatology* 4:107-11

Sugata, F. 1993. [Per oral gallstone dissolution therapy]. *Nippon Rinsho* 51:1785-90

Vlahcevic, Z. R., Hylemon, P. B., Chiang, J. Y. L. 1994. Hepatic cholesterol metabolism. Reven Press Wilson, M. D., Rudel, L. L. 1994. Review of cholesterol absorption with emphasis on dietary and biliary cholesterol. *J Lipid Res* 35:943-55

Wudel, L. J., Jr., Wright, J. K., Debelak, J. P., Allos, T. M., Shyr, Y., Chapman, W. C. 2002. Prevention of gallstone formation in morbidly obese patients undergoing rapid weight loss: results of a randomized controlled pilot study. *J Surg Res* 102:50-6

Yu, L., York, J., von Bergmann, K., Lutjohann, D., Cohen, J. C., Hobbs, H. H. 2003. Stimulation of cholesterol excretion by the liver X receptor agonist requires ATP-binding cassette transporters G5 and G8. *J Biol Chem* 278:15565-70

What is claimed is:

1. A method of treating a subject having cholesterol gallstone disease or at risk of developing such condition, consisting essentially of administering to the subject a therapeutically effective amount of a pharmaceutical composition consisting essentially of ezetimibe (SCH 58235), wherein the ezetimibe increases bile flow in the subject.

2. The method of claim 1, wherein the therapeutically effective amount comprises between 0.1-6.0 mg of ezetimibe per kg body weight of the subject per day.

3. The method of claim 1, wherein the cholesterol gallstone disease is cholelithiasis.

4. The method of claim 1, wherein the ezetimibe increases biliary secretion of compounds in the subject that inhibit the formation of cholesterol gallstones.

5. The method of claim 4, wherein the secreted compounds are bile salts or phospholipids.

6. The method of claim 1, wherein the subject is human.

7. A method treating a subject having cholesterol gallstone disease or at risk of developing such condition, consisting essentially of administering to the subject a pharmaceutical composition consisting essentially of a therapeutically effective amount of exetimibe and an inhibitor of HMG-CoA reductase, wherein the ezetimibe increases bile flow in the subject.

8. The method of claim 7, wherein the inhibitor of HMG-CoA reductase is selected from the group consisting of pravastatin, simvastatin, rosuvastatin, lovastatin, fluvastatin, atorvastatin, and cerivastatin.

9. The method of claim 7, wherein the subject is human.

10. The method of claim 7, wherein the pharmaceutical composition has between 0.1 and 6.0 mg of the ezetimibe per kg body weight and between 10 and 80 mg of the inhibitor of HMG-CoA reductase.

* * * * *